(12) United States Patent
Gonchar

(10) Patent No.: US 11,357,349 B1
(45) Date of Patent: Jun. 14, 2022

(54) DIAPER ASSIST RING

(71) Applicant: Nicolas Gonchar, Brea, CA (US)

(72) Inventor: Nicolas Gonchar, Brea, CA (US)

( * ) Notice: Subject to any disclaimer, the term of this patent is extended or adjusted under 35 U.S.C. 154(b) by 0 days.

(21) Appl. No.: 17/471,085

(22) Filed: Sep. 9, 2021

(51) Int. Cl.
    *A47G 25/90* (2006.01)
    *A61F 13/84* (2006.01)

(52) U.S. Cl.
    CPC .............. *A47G 25/90* (2013.01); *A61F 13/84* (2013.01); *A61F 2013/8476* (2013.01)

(58) Field of Classification Search
    CPC .. A61H 1/00; A61H 3/00; A41B 9/001; A41B 11/14; A41B 2400/44; A41B 9/04; A41B 9/02; A41F 9/025; A41F 9/00; A41F 9/001; A41F 9/02; A47G 25/90; A47G 25/905; A47G 25/907; A47G 25/908; A47G 2200/046; A47G 2400/10; A61F 13/84; A61F 2013/8476; A41D 2400/48; A41D 2400/482; A41D 2200/10; A41D 2400/44
    USPC ........................................................ 223/111
    See application file for complete search history.

(56) References Cited

U.S. PATENT DOCUMENTS

| | | | |
|---|---|---|---|
| 1,468,709 A * | 9/1923 | La Grandeur | B65B 67/1255 294/214 |
| 3,031,683 A * | 5/1962 | Hellwig | D06F 41/00 4/666 |
| 4,130,226 A * | 12/1978 | Farrell | A47G 25/905 223/111 |
| 5,799,654 A | 9/1998 | Kassan | |
| 6,698,044 B2 | 3/2004 | Greenfield et al. | |
| 6,755,198 B2 | 6/2004 | Parker | |
| 7,065,814 B2 | 6/2006 | Rutkowski | |
| 7,921,474 B2 * | 4/2011 | Miller | A41F 9/025 2/338 |
| 8,061,751 B2 * | 11/2011 | Hatcher | B25J 1/04 294/209 |
| 9,907,412 B2 | 3/2018 | Perry | |
| 9,937,086 B2 | 4/2018 | Campbell | |
| 9,980,860 B2 | 5/2018 | Takino | |
| 10,292,876 B2 | 5/2019 | Yoshioka et al. | |
| 10,918,234 B1 * | 2/2021 | Lawver | A47G 25/907 |
| 10,952,542 B2 | 3/2021 | Gundry et al. | |
| 10,980,357 B2 | 4/2021 | Bumside et al. | |
| 10,993,549 B2 | 5/2021 | Karavias | |
| 2008/0169663 A1 * | 7/2008 | Stelzer | A45F 5/1026 294/170 |

(Continued)

*Primary Examiner* — Quang D Thanh
*Assistant Examiner* — Gabriella E Burnette

(57) ABSTRACT

A diaper assist ring has a generic 3-dimensional geometric shape of a circle with a contoured outer perimeter with unique designated/specialized/and customized top front, front and rear markings. The device aligns and holds a diaper to itself by means of elasticity and friction (or clips), to empower users of limited flexibility the possibility of changing their own diapers in a timely and safe manner, warding off the negative ramifications of soiled diapers. The portion of the device that is not deeply inserted into the diaper, is clearly marked and is utilized as a handle. It is made out of hygienically lightweight rigid material(s). The combination of the device with diaper, expands the diaper; to conveniently and safely allow the user's first leg and then the second leg, to be inserted into the diaper's leg openings; in either a sitting or standing position(s); overcoming inherent dangers of loss of balance.

1 Claim, 7 Drawing Sheets

(56) References Cited

U.S. PATENT DOCUMENTS

| | | | |
|---|---|---|---|
| 2009/0120975 A1* | 5/2009 | Schoepe | A47G 25/905 |
| | | | 223/111 |
| 2010/0078450 A1* | 4/2010 | Longhurst | A47G 25/90 |
| | | | 223/111 |
| 2013/0214016 A1* | 8/2013 | Carbray | A47G 25/90 |
| | | | 223/111 |
| 2015/0102617 A1* | 4/2015 | Pluta | E01H 1/1206 |
| | | | 294/1.4 |
| 2015/0190006 A1* | 7/2015 | Fowler | A47G 25/908 |
| | | | 223/113 |
| 2016/0022078 A1* | 1/2016 | Sclafani | A41F 11/16 |
| | | | 2/315 |
| 2016/0198880 A1* | 7/2016 | Bean | A47G 25/905 |
| | | | 223/111 |
| 2017/0105561 A1* | 4/2017 | Cooper | A47G 25/90 |
| 2019/0159618 A1* | 5/2019 | Kucera | A47G 25/90 |
| 2019/0335933 A1* | 11/2019 | Leeper | A47G 25/90 |
| 2021/0282484 A1* | 9/2021 | Sekel | A41F 9/02 |

\* cited by examiner

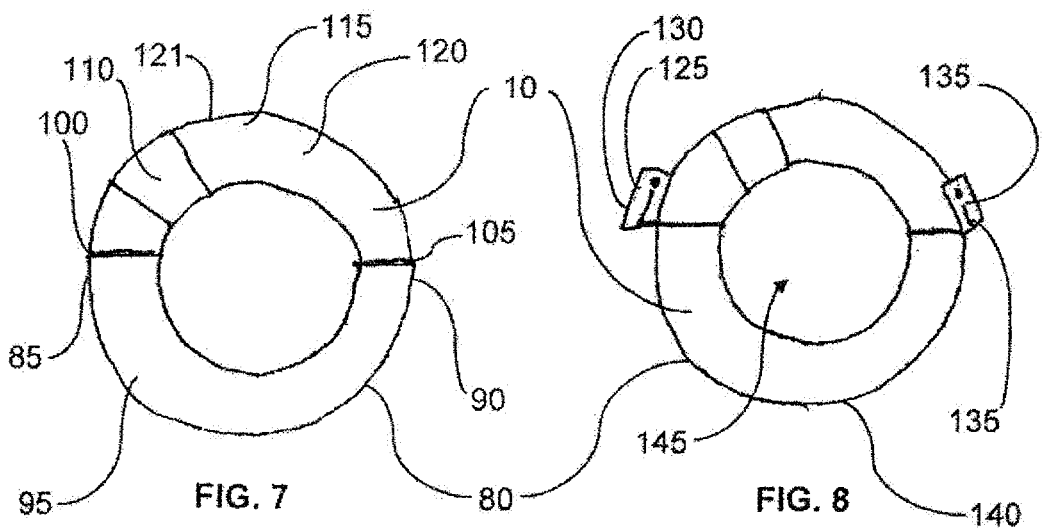
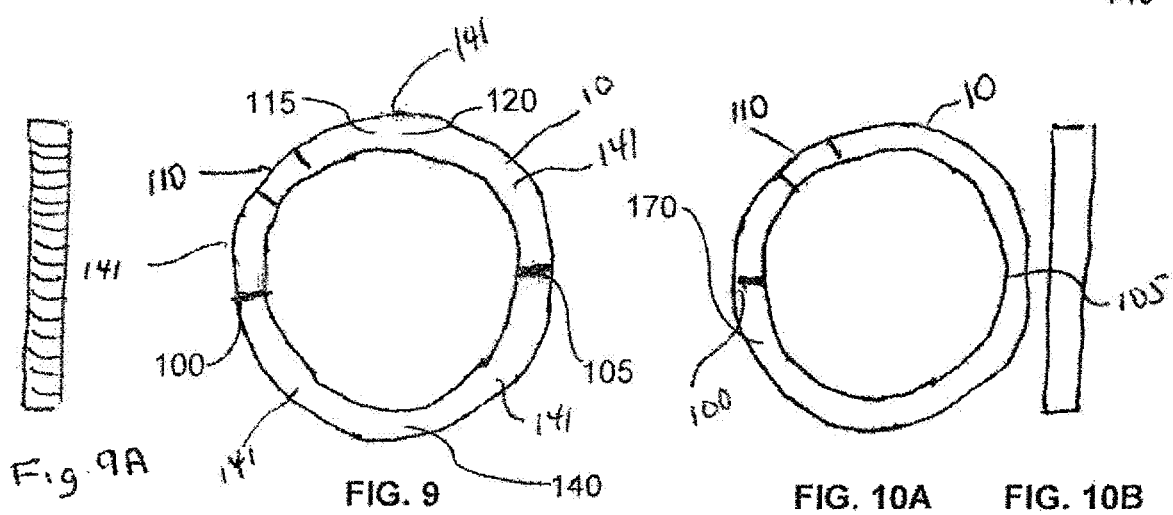
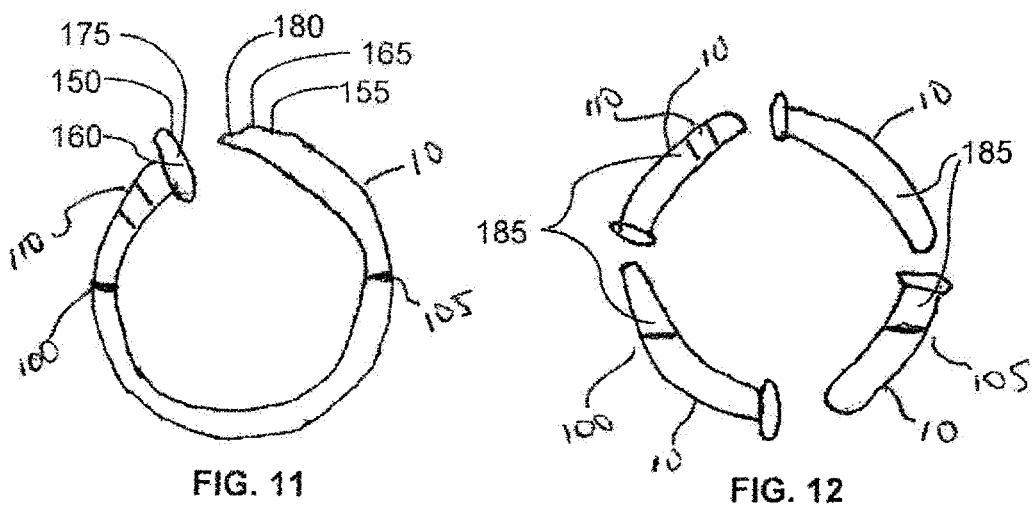

DIAPER ASSIST RING

A diaper assist ring. There are many potential end users who possess various limitations of flexibility throughout their entire bodies, making simple tasks like changing their own diapers, putting on their socks, buttoning their shirts or tying their shoes sometimes dangerous and nearly impossible. Due to the nature of the usual design of the diapers, they are compressed tightly in their packaging and engineered to create a universal fit, by a series of diaper panels and elastic waist and leg bands. Because of initial appearance and flat/shrunken size of the fresh diaper, the end user attempts to fight against its compact design to place it on to their body. Though all end users have varying degrees of physical limitations, the end user frequently labors to get their feet inserted into the leg openings, by forcing and/or contorting their inflexible limbs. It is at this point the end user is exposed to the dangers of balance instability [if standing], extended lack of privacy [nudity] and unwanted leakage due to the awkward repositioning of their contorted body.

The diaper assist ring is designed to aid persons with different and varying degrees of disability, lack of flexibility and/or are of an older age, which require the maintenance of having their diapers changed at varying times throughout the periods of day and night. The end user of the diaper assist ring, would be someone with a combination of any or all of the following issues: limited flexibility, questionable balance and/or limited coordination.

The diaper assist ring can be utilized by persons who are capable of reasonable mobility and activity but cannot be used by all persons whose limitations are beyond (the illusive term) reasonable. Additionally, because the diaper assist ring aids in the changing of the diaper by themselves, the end user has the ability to maintain better hygiene, at their convenience and needs. This timeliness or convenience, aids the end user from languishing in the wetness that may lead to the onset of discomforting sores and rashes. There are no statements by the inventor, that the diaper assist ring can be used by virtually everyone. The diaper assist ring allows the reasonably mobile end users to change their own diapers without sacrificing their loss of balance or personal privacy. The end users should be able to better prevent real dangers of falling or crashing into adjacent hard and ridge objects. The diaper assist ring can be used by reasonably mobile or less dexterous end users, conveniently in the sitting position or in the more precarious (most desirable, due to convenience) standing position.

The diaper assist ring is designed to accommodate end users who use "pullup" style diapers that conform to the end users body style, through a designed pattern of elastic seams and edges. The diaper assist ring has top front indicator band at its top portion of the ring, that indicates both the top and front direction of the ring; this aids the end user in placing the diaper on in the correct position. The end user simply locates the band on the top front, to determine which way to place the diaper on. The diaper assist ring also has front and the rear markings (suggested alignment mark lines) to indicate the placement of the front and the back of the diaper. Initially when the diaper is placed upon the diaper assist ring, it is held in position by the combination of the force created by the extended elastic waistband against the friction of the diaper assist ring surface. However, the diaper assist ring comes in a deluxe model which features clips located near the diaper's front and rear alignment mark lines, to aid persons for who may need added assistance in securing the diaper to the diaper assist ring.

The diaper assist ring allows persons with limited flexibilities and disabilities the freedom, convenience, and confidence (in many cases) to change their own diapers without delay, with significantly reduced risk of falling. The diaper assist ring also reduces the inconvenience or embarrassment of waiting for the help of others. The ease of the use of the diaper assist ring cuts down the time that the end user is exposed to wet diapers, that cause discomfort, rashes, and sores. The diaper assist ring expands and works with the elastic nature of the diaper leg openings, allowing the end users a reasonable solution in creating a clear path to placing their legs into the diaper's leg opening; with lessened difficulty and/or lessened dangerous personal risks.

Basically, the diaper assist ring can be utilized in both the sitting position, by first having the end user sit in a safe and comfortable chair or bedside; and in the standing position, by having the end user find something to balance/support themselves on. The right-handed end user will place the diaper assist ring into the pull up style diaper, noting the top front indicator band of the diaper assist ring and matching the suggested front and rear alignment marks, to correspond to the front and rear of the diaper.

The following is a description in how to use the diaper assist ring. The invention can be utilized in the sitting position, by first having the end user sit in a safe and comfortable chair or bedside. The right-handed end user will place the invention diaper assist ring into the pull up style diaper; noting the front of the invention corresponds to the front top indicator band of the diaper. Later if there is any potential confession to the front versus the back; the end user can simply note the predetermined marking on the invention. Additionally, the invention will have recommended markings for the placement of the front and back of the diaper.

1. The shape/size of the designated diaper assist ring will forcibly expand the diaper's elastic exposing the right leg opening of the diaper; creating an easy and clear path for the right leg to be inserted. The end user holds the combination of the invention and diaper with their left hand, as they guide their right leg with their right hand through the right leg opening of the diaper.

2. The diaper assist ring is then placed on the floor vertically within the diaper, as the end user slides their left leg through a clear path through the left leg opening of the diaper.

3. Once the second leg is inserted, the diaper assist ring is freely released by the over expanded elastic elements of the diaper; as the combination of both legs will expand the elastic larger than the initial tension that was holding the diaper assist ring in place. The end user is able to simply remove the diaper assist ring and pull up the diaper to their waistline.

4. The invention is then stored away, until needed upon future diaper changes. This procedure can also be done, by end users who are left-handed. The process would require the substitution of the word "left" for the word "right" and visa versa within the instructions.

In the event that the end user has the Deluxe version, the end user inserts the front and back waistbands in the designated front and back clips; instead of simply releasing the tension of the diaper's elastic against the friction surface of the diaper assist ring.

The invention can be utilized in the standing position [fastest and most desirable position], by first having the end user stand within a close approximate distance to whatever counter, wall or surface that they can rely on for potential balance. The right-handed end user will place the invention diaper assist ring into the pull up style diaper; noting the front of the invention corresponds to the front indicator band of the diaper.

Additionally, the invention will have recommended markings for the placement of the front and back of the diaper.

1. The shape/size of the designated diaper assist ring will forcibly expand the diaper's elastic exposing the right leg opening of the diaper; creating an easy and clear path for the right leg to be inserted. The end user holds the combination of the invention and diaper with their left hand, as they guide their right leg with their right hand through the right leg opening of the diaper.

2. The diaper assist ring is then placed on the floor vertically within the diaper, as the end user slides their left leg through a clear path through the left leg opening of the diaper.

3. Once the second leg is inserted, the diaper assist ring is freely released by the over expanded elastic elements of the diaper; as the combination of both legs will expand the elastic larger than the initial tension that was holding the diaper assist ring in place. The end user is able to simply remove the diaper assist ring and pull up the diaper to their waistline.

4. The invention is then stored away, until needed upon future diaper changes. This procedure can also be done, by end users who are left handed. The process would require the substitution of the word "left" for the word "right" and visa versa within the instructions.

In the event that the end user has the Deluxe version, the end user inserts the front and back waistbands in the designated front and back clips; instead of simply releasing the tension of the diaper's elastic against the friction surface of the diaper assist ring.

The diaper assist ring is represented as a ring, but the geometric shape of the ring is not limited to a perfect circle. The formation/configuration of the ring would be any geometric shape that has at least 360 degrees, up to and including a megagon. An example of one of the sizes of the ring would be a ring with the diameter 13.5 inches with grip dimension 4.5 inches circumference to (theoretically) accommodate a commercially sized diaper of L/XL. The diaper assist ring will display a top front indicator banding/marking to designate the top front of the ring. The diaper assist ring would also include two additional markings (or clips as stated below) to show the recommended front and back placement of the diapers. The diaper will then be held in place by a combination of elastic tension and friction from the surface of the diaper assist ring.

An alternative deluxe version of the diaper assist ring will have clips to hold the diaper in place at the front and back marks of the diaper assist ring. This version of the diaper assist ring, may be necessary if the combination of the diaper's elastic tension and the diaper assist ring's surface are not compatible or insufficient to hold the diaper firmly in place during the diaper changing process.

Alternatively, attaching aftermarket clips to the original diaper assist ring, could (in some cases) better serve to hold the diaper in place; and would benefit certain/some end users, if they discovered difficulties with the regular version of the diaper assist ring, after initial use. The inventor has considered these aftermarket clips; and they should be included in this same patent application. The aftermarket clips would attach to diaper assist ring and be both removable and adjustable in setting up the front and rear markings.

The term "clips" should include all other like words, such as clips, clasps, hook and pile attachments, buttons, Snap-on buttons, fasteners and similar defined attachment devices/items.

Though current diapers are void of these attachment properties, a diaper manufacturer could produce these features to enhance its diaper's use in combination with the diaper assist ring. As such, this possibility should be included in the scope of this disclosure and this application.

The diaper assist ring could be made out of any variety of reasonably rigid materials, such as Styrofoam, metal, wood, plastic, rubber, tubing, ribbed tubing and/or any combination of all of the above. The materials that the diaper assist ring is made out of should be interpreted as universally, meaning any reasonable singular material or any combination of materials. Thus, any variations in the material construction of the diaper assist ring should not limit the scope of the disclosure or the claims. The applicant believes the best materials are those that are reasonably non-porous, rigid, firm and have (mild) friction (not slippery). The expectations of the user should have a washable surface to be maintained as hygienic, clean, sanitized and generally resistant to germs. It is unexpected and unreasonable that the diaper assist ring will be used in conjunction with soiled diapers. However, there remains the factor that germs from the soiled diaper changing, could ultimately be passed on to the diaper assist ring by the end user's hands, or leakage accidents, sometime during the new diaper change.

The required elements of importance of the diaper assist ring would vary in size to accommodate the various standardized diaper sizes, the end user's ability to keep the diaper assist ring hygienic, and its thickness to aid in the end user's comfort/grip and to maintain friction on the surface; to hold the diapers in place during the actual expansion of the diaper by the diaper assist ring, before, during and after the use of the diaper assist ring to change a diaper.

Although the diaper assist ring is preferably a ring shaped, various shapes may be used, in the formation/configuration of the ring would be a 3-dimensional geometric shape that has at least 360 degrees, up to and including a megagon. Moreover, the diaper assist ring may be a closed loop or an open loop. If an open loop design is used, then it is preferable to have one end (the first end) have a blunt shape and the second end (the second end) has a conical shape; where one end could be inserted into the other to make a closed loop. It should be noted that although the diaper assist ring is shown as a single piece, it is possible to have the outer perimeter formed by a plurality of inter-connecting pieces. Having inter-connecting pieces to form the outer perimeter, the size (the length of the overall diaper assist ring) may be adjusted to better fit the diaper, big and small. The inter-connecting pieces may have two ends, one end designed to accept an end of the adjacently placed piece. Threaded male and female ends may be used, as well as snap on type of connections or magnetic connections.

The diaper assist ring is specifically designed to empower persons with limited disabilities and physical inflexibilities, aiding them to safely and to privately change their own diapers upon the timeliness of their personal needs. The diaper assist ring is specifically designed to accommodate "adult" "pullup style" diapers. These diapers are readily and commercially available through most retail outlets and online, in sizes ranging from x-small to x-large.

It should be stated that since there are other designs of diapers that accommodate sizes beyond ex-large and styles/shapes other than pullup style; it also should be taken for granted that the diaper assist ring could be adapted to and produced in sizes to accommodate these other diaper end users; who typically fall outside the typically sizes of x-small through x-large. The diaper assist ring is not intended for toddlers, as there are no expectations of toddlers changing their own diapers.

Due to the shape of the compressed nature of the pullup diaper, the diaper assist ring accommodates the challenges and problems created by the diaper's design and packaging. Though diaper assist ring works primary for pullup diapers, it could be of benefit for others style of diapers which could be shaped or molded by the end user. The diaper assist ring has the specific intentional purpose of helping those who have difficulties personally dealing with their own diaper changing issue, there may be other forms of clothing that create similar challenges to the same end users.

This invention could serve other garments or forms of clothing as well. This can be examples by "brief style" elastic underwear, certain bathing suits, and miscellaneous other under and outerwear garments. Thus, the diaper assist ring should not be restricted or limited to diapers alone. The diaper assist ring should be liberally used creatively, wherever and whenever an end user deems it necessary, helpful and appropriate.

Any uses other than for diapers, may be identified or accommodated. Examples such as an underwear assist ring, a swimwear assist ring, a sportswear assist ring or a garment assist ring.

These and other features, aspects, and advantages of the diaper assist ring will become better understood with reference to the accompanying specification, writing, drawings, and submission, all of which are incorporated herein.

BRIEF DESCRIPTION OF THE DRAWINGS

These and other features, aspects and advantages of the diaper assist ring will become better understood with reference to the accompanying drawings, wherein:

FIG. 7: a basic version of the diaper assist ring;

FIG. 8: a deluxe version of the diaper assist ring with "clips";

FIG. 9: another version of the diaper assist ring, with ribbed surface texture;

FIG. 9A: a side view of the version of the diaper assist ring shown in FIG. 9, wherein the curved perimeter is ribbed;

FIG. 10A: another version of the diaper assist ring, with flat perimeter;

FIG. 10B: a side view of the version of the diaper assist ring shown in FIG. 10A with flat edge;

FIG. 11: another version of the diaper assist ring with smaller open end adjusting size into larger open end;

FIG. 12: another version of the diaper assist ring where smaller components join together to make one unit of diaper assist ring;

DETAILED DESCRIPTION EMBODIMENTS OF THE INVENTION

A diaper assist ring 10 (as shown in FIG. 7) is described in detail as shown on the Figs.

Figures 1, 2:
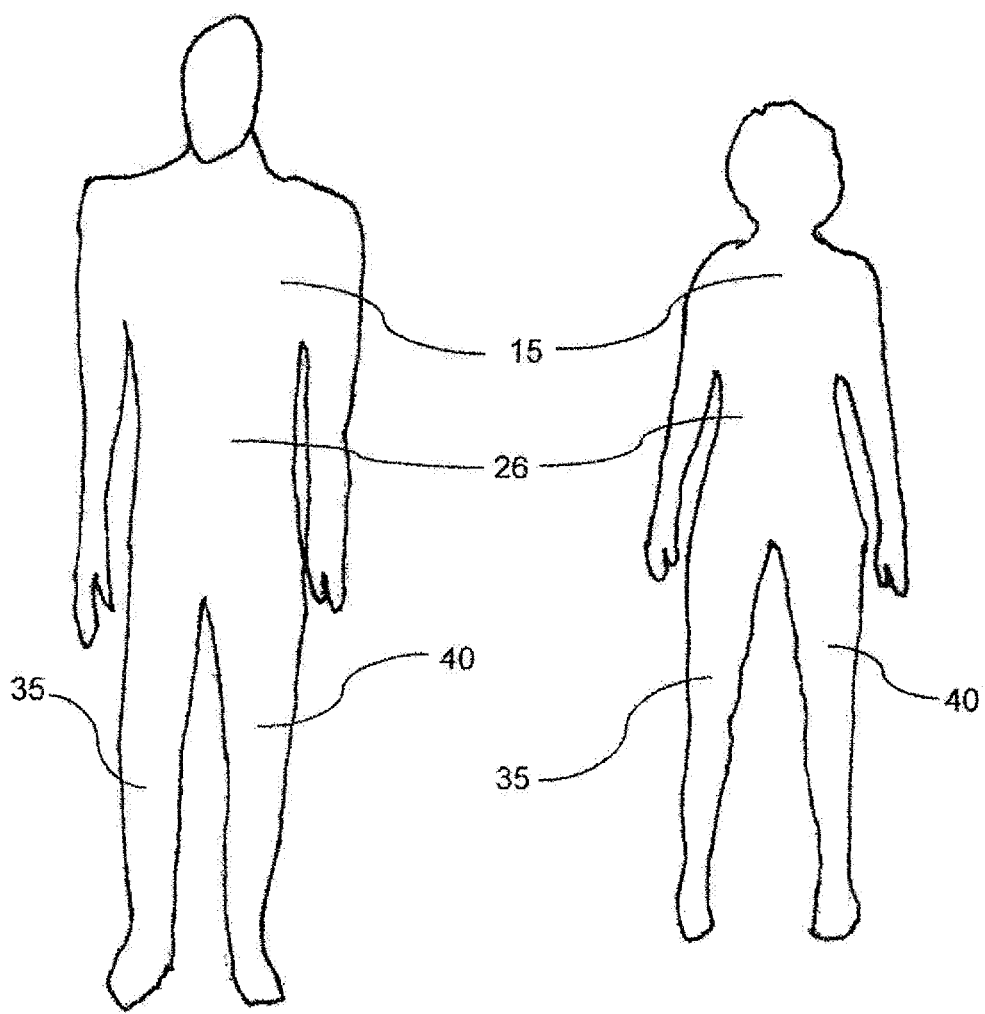
FIG. 1: a man, an end user.
FIG. 2: a woman, also an end user.

FIGS. 1 and 2 show a man and a woman, end users 15, respectively. As men and women age become less flexible or become disabled in some capacity, personal hygiene may become a challenging problem. The diaper assist ring 10 (also described as the "diaper assist device") described herein is to assist users putting on their diapers 20.

Figures 3, 4:
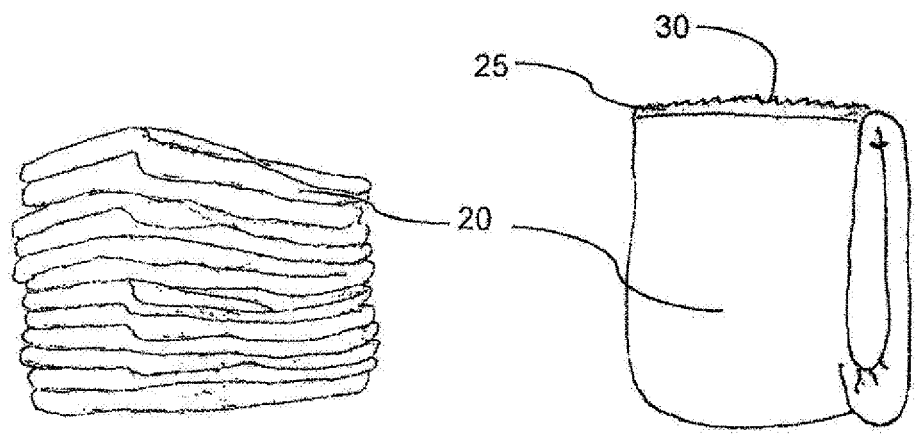
FIG. 3: a set of diapers out of their packaging.
FIG. 4: a diaper with elastic top and elastic leg openings.

FIGS. 3 and 4 show a set of diapers out of their packaging and a diaper 20 with elastic top 25, respectively. Because of the diapers often require tight or snug fit on the waist 26, the top portion 30 of the diaper often has an elastic portion 25 (or a crumpled portion), allowing the elastic portion 25 to stretch and fit the waist 26 of the user 15. Such an elastic top 25 and soft diapers 20 are all neatly crumpled and packaged for packing, but crumpled, packaged diapers 20 often cause a problem for seniors, handicapped, or disabled persons. In order to put on a diaper 20, such a person would have to hold on to the diaper 20, holding and stretching the diaper 20, while trying to put the legs 35, 40 through the diaper leg openings 55, 50 (a left diaper leg opening 55 and a right diaper leg opening 50, shown on FIG. 5), risking the loss of balance causing dangerous situations. Putting on diapers 20 is a problem for certain seniors and disabled which is a difficult and maybe even be a dangerous task, that it might require assistance.

Figures 5, 6:
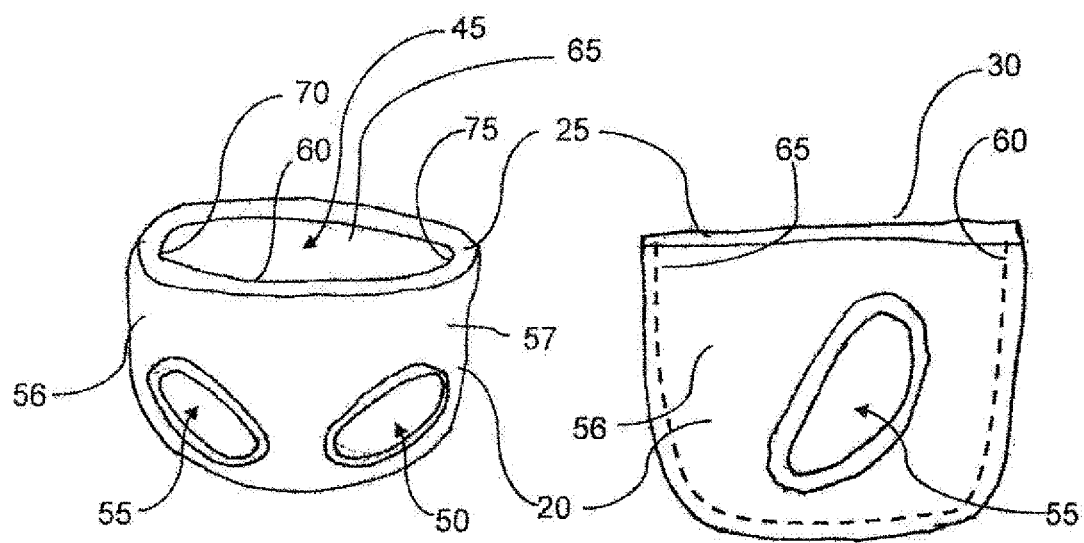
FIG. 5: a front view of a diaper with elastic top and elastic leg openings.
FIG. 6: a side view of a diaper with elastic top and left leg opening.

FIG. 5 shows a front view of an expanded diaper 20 with its right side 56 and its left side 57, and FIG. 6 show the left side view of an expanded diaper 20. FIG. 5 shows an expanded diaper 20 with an elastic top 25 with an upper opening 45, a left diaper leg opening 50 for inserting the user's right leg and a left diaper leg opening 55 for inserting the user's left leg 40. The elastic top 25 forms an upper opening 45, exposing an inner-front section 60, an inner-rear section 65, a right-inside 70, and a left-inside 75 of the diaper.

FIG. 6 shows the right side 56 of the diaper and the right diaper leg opening 55 for inserting the user's left leg 40.

FIG. 7 shows a version of the diaper assist ring 10. The diaper assist ring 10 has an outer perimeter 80 having a front section 85 and a rear section 90. The outer perimeter 80 defines the shape of the diaper assist ring 10. The diaper assist ring 10 is a ring shape. The diaper assist ring 10 is marked with a front-end marking 100 to indicate the front section marking 85 of the diaper assist ring 10 and a rear-end marking 105 to indicate the rear section 90 of the diaper assist ring 10. The diaper assist ring 10 is also marked with has top front band indicator marking 110 to indicate the top front upper side 115 of the diaper assist ring 10 so the user is ensured of holding the diaper assist ring 10 with the proper orientation; the front-end marking 100 toward the front of the user and the rear-end marking 105 toward the back of the user. It is imperative to have the upper marking 110 placed in between the portion of the outer perimeter 80 used as a handle 120 and the front-end marking 100, at the upper-front side 121 of the outer perimeter 80, so the user can see the diaper assist ring 10 is properly oriented while the user is holding the diaper assist ring 10 during the changing of the diaper. The outer perimeter 80 is held as a handle 120 so the diaper assist ring 10 is placed in a diaper 20 with the front section 85 placed at the inner-front section 60 of the diaper 20 and the rear section 90 is placed at the inner-rear section 65 of the diaper 20, allowing a right leg 35 to be inserted in between the diaper assist ring 10 and a right-inside 70 of the diaper 20, through the right diaper opening 50, and allowing a left leg to be inserted in between the diaper assist ring 10 and a left-inside 55 of the diaper 20, through the left diaper leg opening 50.

FIG. 8 shows deluxe version of the diaper assist ring 10. This version of the diaper assist ring 10 has a front-attaching article 125, shown as a clip 130, located on the front section 85, and a rear-attaching article 135, also shown as a clip 130, located on the rear section 90. FIG. 8 shows the front-attaching article 125 located on or near the front-end marking 100, and the rear-attaching article 135 located on or near the rear-end marking 105. The inventor believes this version, of using clips, could benefit some end users when the diaper 20 and the diaper assist ring 10 are completely compatible.

FIG. 9 and FIG. 9A shows another version of the diaper assist ring 10 the makings 110 top front indicator band, 100 right front alignment mark and 105 rear alignment mark, with an upper side 115 and a lower side 140. In this version, the surface of the diaper assist ring has a ribbed surface FIG. 9A 141 to offer greater friction surface to the tension produced by the elastic of the diaper 25. FIG. 9A is the sideview of FIG. 9, showing the ribbed texture of the surface 141, available in both molded and tubular forms.

FIG. 10A shows another version of the diaper assist ring 10, with the makings 110 top front indicator band, 100 right front alignment mark and 105 rear alignment mark, and FIG. 10B is a side view of the version of the diaper assist ring 10 shown in FIG. 10A. The diaper assist ring 10 shown here is in a shape of a ring. It has a smooth surface or a textured surface. It may also have a round cylindrical cross section or a various shaped cylindrical cross section, including having straight edges. FIG. 10B shows that the diaper assist ring 10 shown has straight edges, such that a cross section of the diaper assist ring 10 along the radius has a substantially square shape.

FIG. 11 shows another version of the diaper assist ring 10 with the makings 110 top front indicator band, 100 right front alignment mark and 105 rear alignment mark. In this version, the outer perimeter 80 has a first end 150 and a second end 155, the first end has a blunt shape 160 and the second end has a conical shape 165. 165 is inserted into 160 to close the loop to the required size needed for the diaper assist ring 10 to match the size of the diaper 20. The inventor prefers the outer perimeter 80 forming a closed loop 170. It should be noted that the blunt end 175 may be designed to accept the conical shaped end 180, by having male-female threads, hook-and-pile attachments, click-and-lock attachments, or other commercially acceptable methods. Such a design would require a portion of the outer perimeter to be substantially flexible so that the outer perimeter 80 may form a closed loop.

FIG. 12 shows another version of the diaper assist ring 10 with the makings 110 top front indicator band, 100 right front alignment mark and 105 rear alignment mark. In this version, the outer perimeter 80 is formed by a plurality of inter-connecting arc-shaped pieces 185. Each of the inter-connecting arc-shaped pieces 185 has one end designed to accept a joining end of the other inter-connecting arc-shaped piece.

Figure 13:
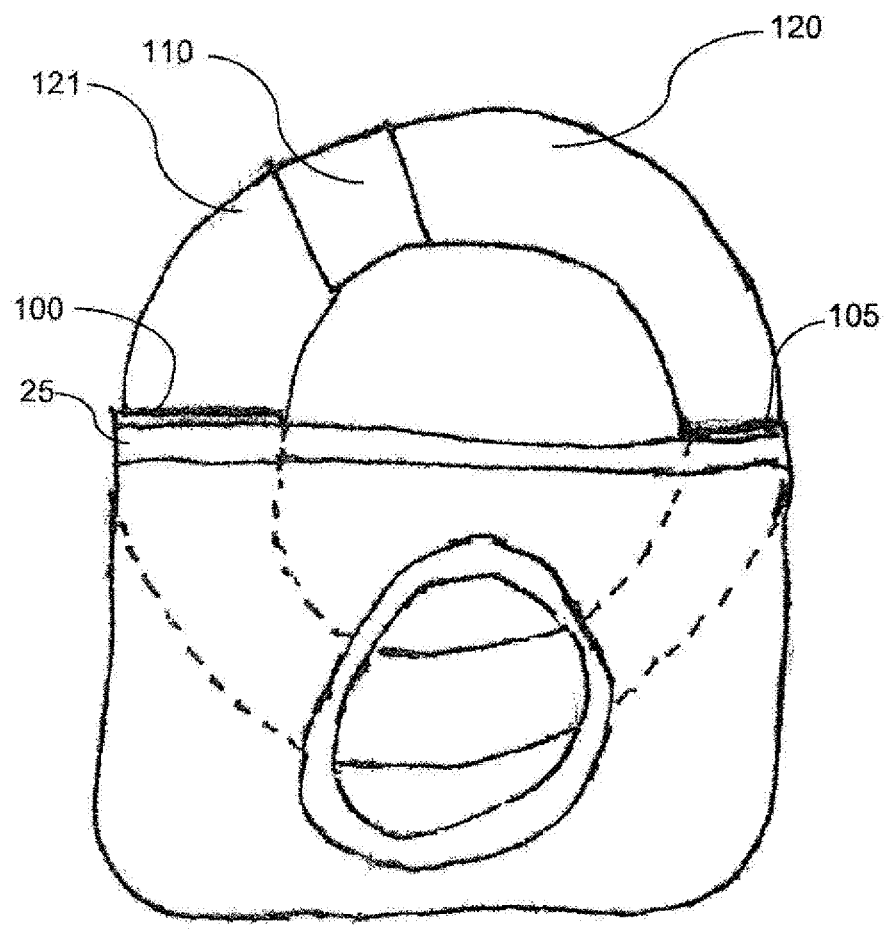
FIG. 13: the diaper assist ring inserted in a (expanded) diaper.

FIG. 13 show the diaper assist ring 10 inserted in a diaper 20. The diaper 20 is stretched so that the elastic top accepts the diaper assist ring fittingly (or snuggly or tightly). The inner-front section 25 of the diaper 20 aligns with the front-end marking 100 of the diaper assist ring 10 and the inner-rear section 25 of the diaper 20 aligns with the rear-end marking 105 of the diaper assist ring 10. As shown in FIG. 13, the diaper assist ring 10 is inserted vertically, with the upper side 120 towards the head of the user, visible to the user. The top front marking 110 is visible to the user indicating that the diaper assist ring 10 is properly positioned on the front of the diaper 20.

Figure 14:
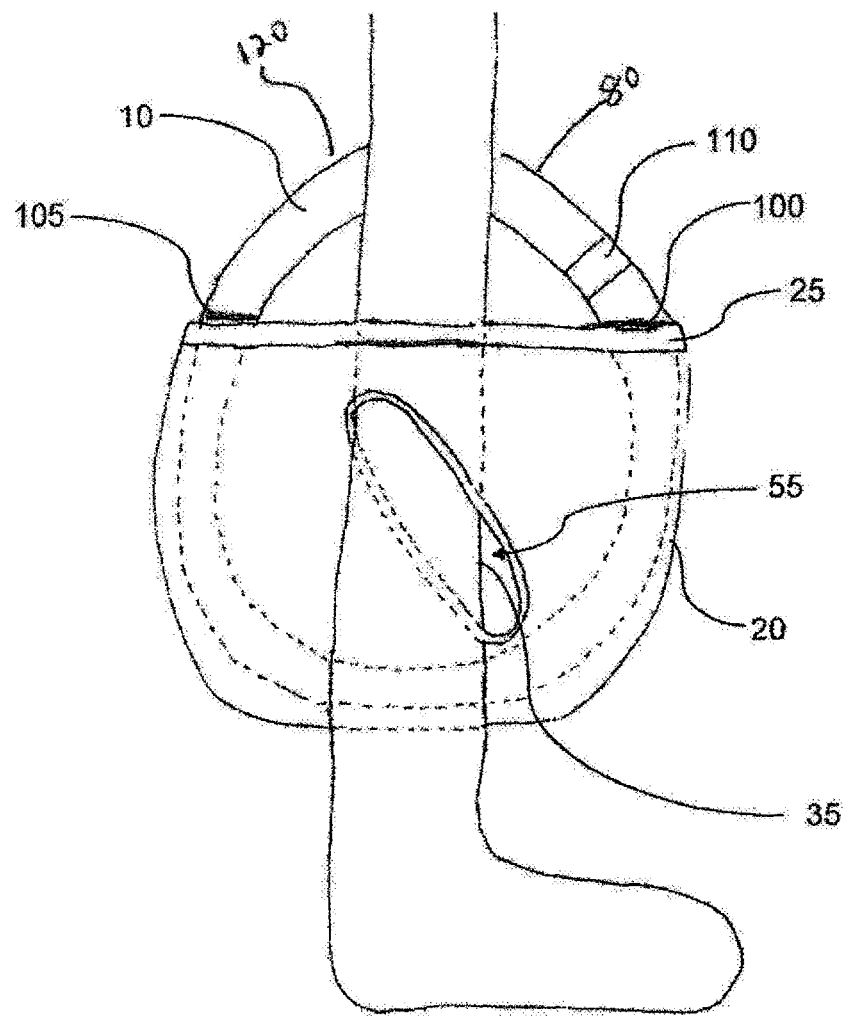
FIG. 14: the diaper assist ring inserted in a (expanded) diaper with a user's right leg inserted into the diaper, through the right-side leg opening of the diaper.

FIG. 14 shows the diaper assist ring 10 with the makings 110 top front indicator band, 100 right front alignment mark and 105 rear alignment mark, shows the diaper 20 with an end user's right leg 35 inserted into the diaper 20, through the right diaper opening 55 of the diaper 20.

Figure 15:
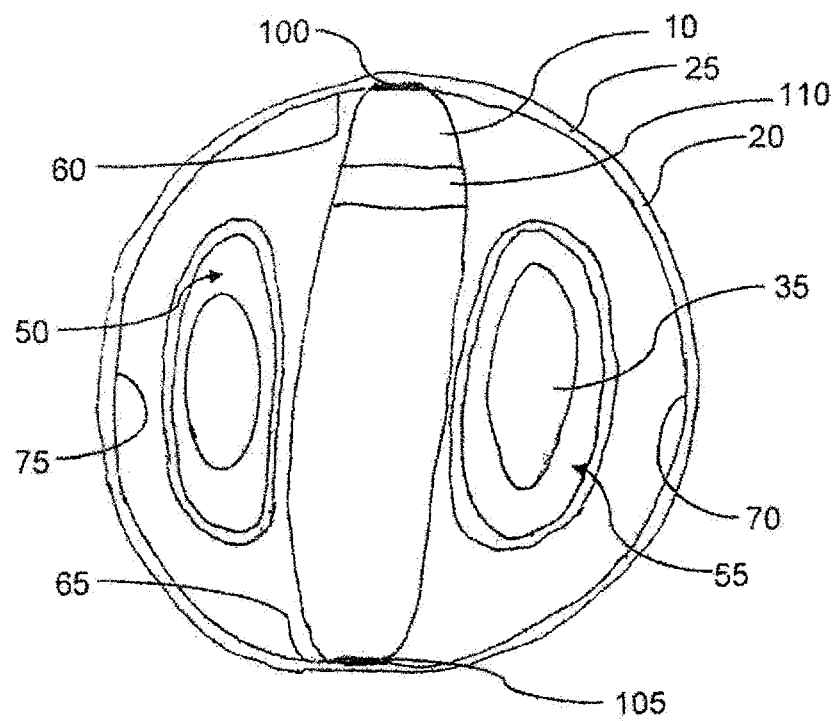
FIG. 15: a top view of the diaper assist ring with user's right leg (only) inserted into the diaper's right leg opening.

FIG. 15 is a top view of the diaper assist ring 10 with the makings 110 top front indicator band, 100 right front alignment mark and 105 rear alignment mark. inserted in the diaper 20 with the user's right leg 35 (only) through the right diaper leg opening 55 of the diaper 20, respectively. The diaper assist ring 10 holds the elastic top 25 along with the top portion 30 expanded across the diaper 20 wide enough that the user's right leg 35 can be inserted into the diaper 20, in between the diaper assist ring 10 and directly into the right leg opening 55 of the diaper 20.

Figure 16:
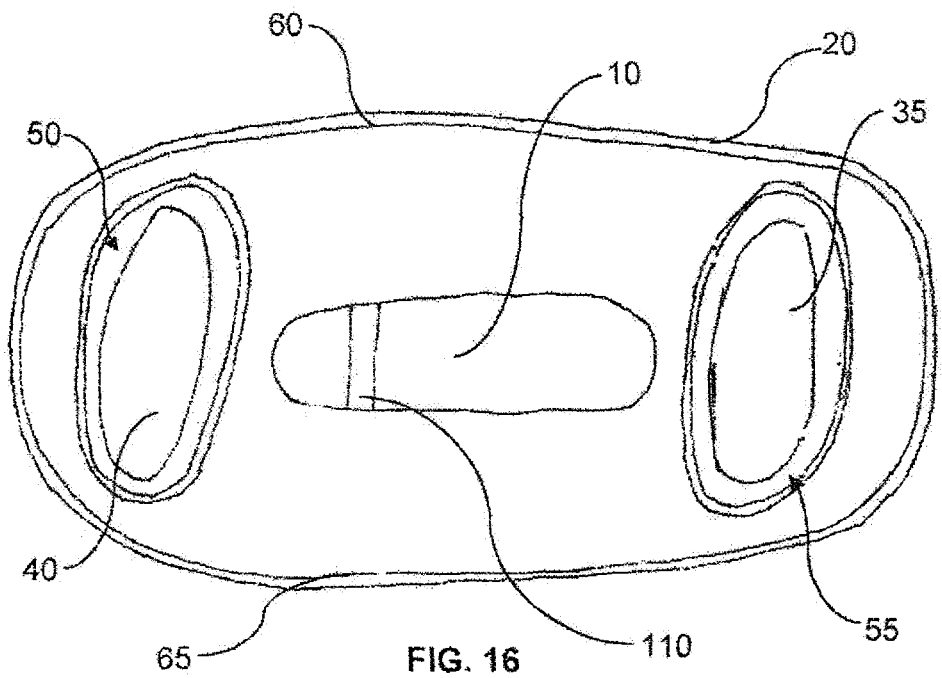
FIG. 16: a top view of the diaper assist ring with the user's both legs inserted in the diaper through the right leg diaper opening and the left diaper opening of the diaper, respectively; the diaper is stretched by the user's stance and the diaper assist ring become free of tension and then the end user simply and conveniently removes the free-floating loose diaper assist ring.

FIG. 16 is a top view of the diaper assist ring 10 with the makings 110 top front indicator band, 100 right front alignment mark and 105 rear alignment mark, after the left leg 40 has been inserted into diaper leg opening 50. The diaper 20 is now expanded by the width of the end user's stance and the diaper assist ring 10 is release by the lack of contact with diaper's elastic forces. FIG. 16 shows the diaper assist ring 10 is free of tension and is released and floating freely, with the appearance that it has rotated 90 degrees counterclockwise as the tension is released. As the diaper assist ring 10 is released, the user can easily remove the diaper assist ring 10 from the diaper 20 and store it away.

Figure 17:
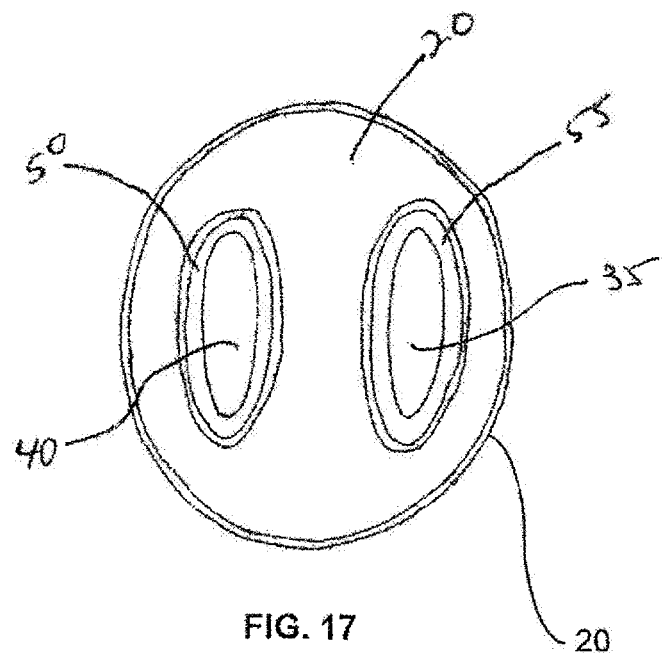
FIG. 17: a top view of the diaper with the user's right leg and the left leg inserted into the diaper, through the right diaper opening and the left diaper opening of the diaper, respectively, with the diaper assist ring removed with the diaper already pulled up upon the end user's waist.

FIG. 17 show a top view of the diaper 20 with the user's right leg 35 and the left leg 40 inserted into the diaper 20, through the right diaper leg opening 55 and the left diaper leg opening 50 of the diaper 20, respectively, with the diaper assist ring removed.

Figure 18:
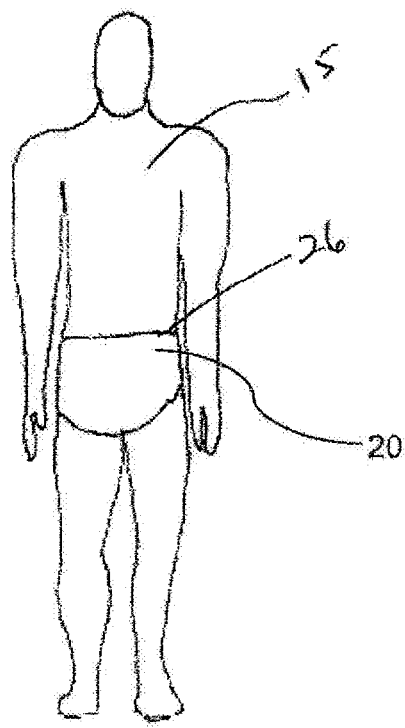
FIG. 18: the user wearing a diaper, pulled up to their waistband.

FIG. 18 shows the user 15 with the diaper 20 properly placed at the user's waist 26.

While the description, drawings, and references have presented, shown, and described with reference to different embodiments thereof, it will be appreciated by those skilled in the art that variations in form, detail, compositions, and operation may be made without departing from the spirit and scope of the disclosure.

What is claimed is:
1. A device for assisting the donning of a diaper, said device consisting of:

a rigid, non-porous ring having an unbroken contoured outer perimeter in the shape of a circle; said outer perimeter having:
- an upper surface, a lower surface, a front section, and a rear section;
- a front marking on the front section of the outer perimeter that is configured to be aligned with a front end of the diaper;
- a rear marking on the rear section of the outer perimeter that is configured to be aligned with a rear end of the diaper;
- a front gripping mechanism on the front section of the outer perimeter that is configured to be affixed to the front end of the diaper; and
- a rear gripping mechanism on the rear section of the outer perimeter that is configured to be affixed to the rear end of the diaper;

wherein the rigid, non-porous ring is configured to be placed into the diaper perpendicular to a diaper's waist opening such that the front and rear gripping mechanisms are affixed to the front and rear end of the diaper respectively and that the lower surface is inserted into the diaper while the upper surface remains located above the waist opening.

\* \* \* \* \*